(12) United States Patent
Murray et al.

(10) Patent No.: US 7,411,074 B2
(45) Date of Patent: *Aug. 12, 2008

(54) PROCESS AND INTERMEDIATES FOR THE PREPARATION OF THE THIENOPYRROLE DERIVATIVES

(75) Inventors: Paul Murray, Bristol (GB); Jeremy Stephen Parker, Bristol (GB); Paul Schofield, Macclesfield (GB); Andrew Stocker, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 476 days.

This patent is subject to a terminal disclaimer.

(21) Appl. No.: 10/528,974

(22) PCT Filed: Sep. 29, 2003

(86) PCT No.: PCT/GB03/04217

§ 371 (c)(1),
(2), (4) Date: Mar. 23, 2005

(87) PCT Pub. No.: WO2004/031194

PCT Pub. Date: Apr. 15, 2004

(65) Prior Publication Data

US 2006/0035953 A1    Feb. 16, 2006

(30) Foreign Application Priority Data

Oct. 3, 2002    (GB) .................... 0222912.8

(51) Int. Cl.
C07D 495/04    (2006.01)
(52) U.S. Cl. ........................ 548/453; 548/452
(58) Field of Classification Search ............ 548/452, 548/453
See application file for complete search history.

(56) References Cited

U.S. PATENT DOCUMENTS

| | | |
|---|---|---|
| 2004/0048878 A1 | 3/2004 | Cai et al. |
| 2004/0142938 A1 | 7/2004 | Sher et al. |
| 2004/0220229 A1 | 11/2004 | Bussolotti et al. |

FOREIGN PATENT DOCUMENTS

| | | |
|---|---|---|
| EP | 1088824 A2 | 4/2001 |
| EP | 1136071 A3 | 3/2003 |
| EP | 1 340 500 A1 | 9/2003 |
| JP | 2004196702 A | 7/2004 |
| SU | 364613 | 12/1972 |
| WO | WO-1994/18196 A1 | 8/1994 |
| WO | WO-01/28993 A | 4/2001 |
| WO | WO-2001/28993 A2 | 4/2001 |
| WO | 01/32622 A1 | 5/2001 |
| WO | WO-2002/06246 A1 | 1/2002 |
| WO | WO-2002/20530 A1 | 3/2002 |
| WO | 03/072570 A1 | 9/2003 |
| WO | WO-2003/074484 A1 | 9/2003 |
| WO | WO-2003/074485 A2 | 9/2003 |
| WO | WO-2003/074513 A2 | 9/2003 |
| WO | WO-2003/074517 A1 | 9/2003 |
| WO | WO-2003/074531 A1 | 9/2003 |
| WO | WO-2003/074532 A1 | 9/2003 |
| WO | WO-2003/091213 A1 | 11/2003 |
| WO | 2004/031193 A1 | 4/2004 |
| WO | WO-2004/041780 A2 | 5/2004 |
| WO | WO-2004/058715 A1 | 7/2004 |
| WO | 2004/092158 A1 | 10/2004 |
| WO | WO-2004/113345 A1 | 12/2004 |
| WO | 2005/013975 A1 | 2/2005 |
| WO | 2005/013981 A1 | 2/2005 |
| WO | 2005/018637 A1 | 3/2005 |
| WO | 2005/019172 A1 | 3/2005 |
| WO | 2005/020985 A1 | 3/2005 |
| WO | 2005/020986 A1 | 3/2005 |
| WO | 2005/020987 A1 | 3/2005 |

OTHER PUBLICATIONS

Freeman, S., et al., "Effect of Glucose on Rat and Human Liver Glycogen Phosphorylasea Activity and Potency of a Glycogen Phosphoylase Inhibitor," Diabetes, 52, Supp., 1470-P, A340 (2003).

Turnbull, A., et al., "Pharmacological Inhibition of Glycogen Phosphorylase (GP) Lowers Plasma Glucose in Rat Models of Type 2 Diabetes," Diabetes, 52, Supp., 1485-P, A343 (2003).

(Continued)

Primary Examiner—Golam M Shameem

(57) ABSTRACT

A process for preparing a compound of formula (I) where $R^4$ and $R^5$ are as defined in the specification; and $R^6$ is hydrogen or a protecting group, which process comprises cyclisation of a compound of formula (II) where $R^4$, $R^5$ and $R^6$ are as defined in relation to formula (I), and $R^7$ is nitrogen-protecting group, and removing the group $R^7$—, and thereafter if desired or necessary, removing any protecting group $R^6$ to obtain the corresponding carboxylic acid. Novel intermediates and the use of the products in the preparation of pharmaceutical compounds is also described and claimed.

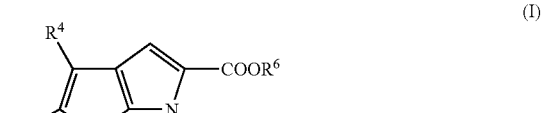

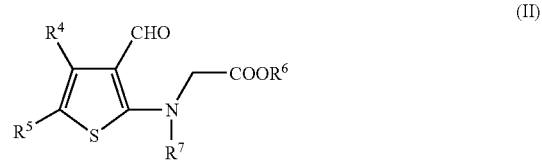

5 Claims, No Drawings

OTHER PUBLICATIONS

Birch, A., et al., "Novel Thienopyrrole Glycogen Phosphorylase Inhibitors: In Vitro SAR and Crystallographic Studies," Poster, Cambridge Med Chem Symposium (Sep. 2003).

Hudson, S., et al., "The effect of a glycogen phosphorylase inhibitor upon muscle fatigue in anaesthetised rats," J. Physiol., 539:52-53 (2002).

Vertigan, H. et al. "Impact of cell glycogen content on modulation of hepatocyte glucose metabolism by pharmacological agents", EASD Munich (2004).

Bartlett, J. et al. "In Vitro and In Vivo Profile of Gpi688, a Novel, Potent Inhibitor of Glycogen Phosphorylase", ADA San Diego (2005).

Simpson, I. et al. "Novel Orally Active Amino-indan Inhibitors of Glycogen Phosphorylase", Cambridge Med Chem Conference, (Sep. 2005). Poster EOM.

Green, A R. et al. "The Glycogenic Action of Protein Targeting to Glycogen in Hepatocytes Involves Multiple Mechanisms Including Phosphorylase Inactivation and Glycogen Synthase Translocation", J Biol Chem, 279(45), 46474-46482 (2004).

Roberts, P A. et al. "The temporal relationship between glycogen phosphorylase and activation of the pyruvate dehydrogenase complex during adrenaline infusion in resting canine skeletal muscle", J Physiology-London 545(1), 297-304 (2002).

PCT/GB2003/004217 Search Report Jun. 8, 2004.

Meth-Cohn et al., "The preparation and formylation of 2-acetamidothiophenes," Synthesis 2:133-135 (1980).

Nakamura, "Construction of heterocyclic compounds by use of alpha-diazaphosphonates: new one-pot syntheses of indoles and isocoumarines," Organic Letters 4(14)2317-2320 (2002).

Shvedov et al., "2-Aminothieno '2,3-blpyridine derivatives," Database CA 'Online! Chemical Abstracts Service Database accession No. 78:159580 XP002266826 (1972).

Sugiyama et al., "Condensed thienopyridines. IV. Synthesis and gastric antisecretory activity of 2,3-dihydro-5H-oxazolothienopyrimidine derivatives," Chemical & Pharmaceutical Bulletin 37(10):2171-2722 (1989).

Sugiyama et al., "Condensed thienopyrimidines. 5. Studies on the thermal cyclization of various ortho-formylthiophenecarbamates with ethanolamine," Heterocycles 29(7):1317-1323 (1989).

Adams et al., "4-Amino-4,5-dihydrothiophene-2-carboxylic acid," J. Org. Chem. 50:2730-2736 (1985).

Binder et al., "Eine einfache herstellungsmethode fur 2-aminothiophene," Synthesis Communications 4:255-256 (1977).

Binder et al., "Thiopen als strukturelement physiologisch aktiver substanzen, 8. mitt. 1H5H-imidazo[1,2-a]thieno[3,4-d]pyrimidin-2(3H-one," Arch Pharm. 314:556-564 (1981).

Bjork et al., "Improved syntheses of thieno[2,3-b]- and [3,2-b]-fused naphthyridines," J. Heterocyclic Chem. 32:751-754 (1995).

Boger et al., "Total synthesis of distamycin A and 2640 analogues: A solution-phase combinatorial approach to the discovery of new, bioactive DNA binding agents and development of a rapid, high-throughput screen for determining relative DNA binding affinity or DNA binding sequence selectivity," J. Am. Chem. Soc. 122:6382-6394 (2000).

Brugier et al., "α-Substitution of β-thienylcarbamates: alkylation, vinylation and Pd-catalyzed coupling reactions," Tetrahedron 56:2985-2993 (2000).

Brugier et al., "Studies on the reactivity of N-(3-thienyl)carbamates," J. Chem. Soc., Perkin Trans. 1:37-43 (2001).

Brugier et al., "Synthesis and reactivity of alkyl (4-aminothien-3-yl)carbamates," Tetrahedron 53(30):10331-10344 (1997).

Brunnett et al., "Heterocyclic amines. IV. Urethan and urea derivatives of 3-aminothiophene (1)," J. Heterocyclic Chem. 5(3):417-418 (1968).

Carroll et al., "Competitive ortho metalation effects: the kinetic and thermodynamic lithiation of 3-(*tert*-Butoxycarbonyl)amino-4-caromethoxythiopene," Tetrahedron Letters 38(15):2637-2640 (1997).

Eras et al., "Reactivity of theinopyrroles. synthesis of isomeric nitro and bromothienopyrroles," J. Heterocyclic Chem. 21:215-217 (1984).

Galvez et al., "Synthesis of isomeric β-haloethylthienopyrroles," J. heterocyclic Chem. 21, 393-395 (1984).

Galvez et al., "Synthesis of thiophenedicarbonyldiazides and Di-*t*-butyl thiophendicarbamates," J. Heterocyclic Chem. 23:1103-1108 (1986).

Jones et al., "The Vilsmeier reaction of fully conjugated carbocycles and heterocycles," Organic Reactions 49:1-39 (1997).

Kobayashi et al., "Heterocyclic sulfonyl compounds and activated blood coagulation factor X (FXa) inhibitors containing them," Chemical Abstracts XP002267904 & JP 2001 294572 (2001).

Linda et al., "The mechanism of the Vilsmeier-Haach reaction. Part III. Structural and solvent effects," J. Chem. Soc. Perkins Trans II, 1610-1612 (1974).

Marques et al., "Toward an understanding of the chemical etiology for DNA minor-groove recognition by polyamides," Helvetica Chimica acta 85:4485-4517 (2002).

Martin et al., "Nucelar magnetic resonance investigations of carbonium ion intermediates. Part II. Exchange reactions in chloro-iminium salts (Vilsmeier-Haack reagents)," Journal Chem. Soc., Perkins Trans II 642-646 (1974).

Martin et al., "Recherches sur la reaction de vilsmeier-haack etude du mecanisme de formation du complexe par des mesures cinetiques en resonance magnetique nucleaire," Tetrahedron Letters 58:5061-5064 (1970).

Meth-Cohn et al., "A versatile new synthesis of quinolines and related fused pyridines. Part II.," Tetrahedron Letters 33:3111-3114 (1979).

Meth-Cohn et al., "A versatile new synthesis of quinolines and related fuses pyridines. Part 7. The conversion of acetamidothiophens into thienopyridines," Journal Chem. Soc., Perkins Trans. I 1531-1536 (1981).

Meth-Cohn et al., "A versatile new synthesis of quinolines, thienopyridines and related fused pyridines," Tetrahedron Letters 23:2045-2048 (1978).

Rajanna et al., "Kinetics adn mechanism of vilemeier-haach synthesis of 3-formyl chromones derived from o-hydroxy aryl alkyl ketones: A structure reactivity study," Tetrahedron 52(10):3669-3682 (1996).

Seela et al., "168. Synthesis of 2'-deoxyribofuranosides of 8-Aza-7-deazaguanine and related pyrazolo[3,4-d]pyrimidines," Helvetica Chimica Acta 69:1602-1613 (1986).

Shinkwin et al., "Synthesis of thiophenecarboxamides, thieno[3,4-c]pyridin-4(5H)-ones and Thieno[3,4-d]pyrimidin-4(3H)-ones and preliminary evaluation as inhibitors of poly(ADP-ribose)polymerase (PARP)," Bioorganic & Medicinal Chemistry 7:297-308 (1999).

Shvedov et al., 2-Aminothieno '2,3-b]pyridine derivatives, Chemical Abstracts, XP002266826 & SU364613 (1973).

Soth et al., "Recherches en serie heterocyclique. XXIX. Sur des voies d'acces a des thieno, selenolo, furo et pyrrolopyrroles," Canadian Journal of Chemistry 56(6):1429-1434 (1978).

Stanetty et al., "Herbizide thienylharnstoffe, I," Monatshefte fur Chemie 120:53-63 (1989).

Sugiyama et al., "Condensed thienopyrimidines. IV. Synthesis and gastric antisecretory activity of 2,3-dihydro-5H-oxazolothienopyrimidine derivatives," Chemical & Pharmaceutical Bulletin 37(10):2171-2722 (1989).

Szabo et al., "Experimental and theoretical study of orientation in the nitration of dithieno[3,4-b:3',4'-d]pyridine," J. Organic Chem 56:1590-1596 (1991).

PROCESS AND INTERMEDIATES FOR THE PREPARATION OF THE THIENOPYRROLE DERIVATIVES

RELATED APPLICATIONS

This application is a national stage filing under 35 U.S.C. 371 of International Application PCT/GB2003/004217, filed Sep. 29, 2003, which claims priority from United Kingdom Patent Applications No. 0222912.8, filed Oct. 3, 2002, the specifications of each of which are incorporated by reference herein. International Application PCT/GB2003/004217 was published under PCT Article 21(2) in English.

The present invention relates to a novel process for preparing intermediates for therapeutically effective compounds, together with novel intermediates for use in the process.

Compounds with glycogen phosphorylase activity are described in WO 02/20530. These compounds have a general formula which may be represented as formula (A)

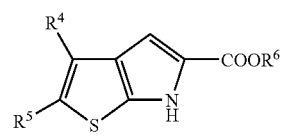

(A)

where X, Y and Z is selected from inter alia —$CR^4$=$CR^5$—S—, $R^4$ and $R^5$ are independently selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N,—($C_{1-6}$alkyl)$_2$sulphamoyl, $C_{1-6}$alkylsulphonylamino and $C_{1-6}$alkylsulphonyl-N—($C_{1-6}$alkyl)amino; n is 0-4, and $R^1$, $R^2$ and $R^3$ are various specified organic groups.

These compounds are generally prepared by a reacting an acid of formula (B)

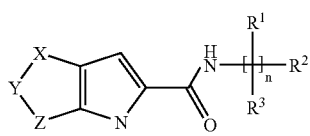

(B)

with an appropriate amine. Acids of formula (B) are prepared according to the following scheme:

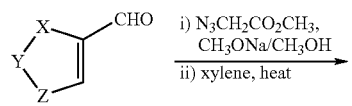

i) $N_3CH_2CO_2CH_3$, $CH_3ONa/CH_3OH$
ii) xylene, heat

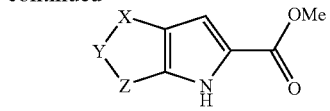

(B)

However, this process is difficult to effect as it may proceed explosively.

The applicants have found an improved process for the production of certain intermediates.

The present invention provides a process for preparing a compound of formula (I)

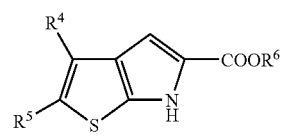

(I)

where $R^4$ and $R^5$ are independently selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N,—($C_{1-6}$alkyl)$_2$sulphamoyl, $C_{1-6}$alkylsulphonylamino and $C_{1-6}$alkylsulphonyl-N—($C_{1-6}$alkyl)amino; and $R^6$ is hydrogen or a protecting group, which process comprises cyclisation of a compound of formula (II)

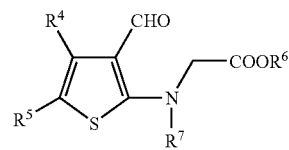

(II)

where $R^4$, $R^5$ and $R^6$ are as defined in relation to formula (I) and $R^7$ is a nitrogen-protecting group, and removing protecting group $R^7$, and thereafter if desired or necessary, removing any protecting group $R^6$ to obtain the corresponding carboxylic acid.

Cyclisation is suitably effected in an organic solvent such as methanol or dimethylformamide (DMF) in the presence of a base. Suitable bases include particularly strong bases such as an alkali metal alkoxide, for instance sodium methoxide, but also weaker bases such as alkali metal carbonates like potassium carbonate. The reaction is suitably carried out at a broad range of temperatures, for example of from ambient temperature to 70° C., and conveniently at the reflux temperature of the solvent. Under these conditions, $R^7$ is generally removed in the same reaction step. Depending upon the nature of the group employed however, it might be necessary to remove $R^7$ in a subsequent step, for example by acid or base hydrolysis reactions.

Acid hydrolysis reactions may be carried out using conventional methods, and in particular using acids such as trifluoromethanesulphonic acid, acetic acid or hydrochloric acid. Base hydrolysis reactions are suitably effected in the presence of bases, such as alkali metal hydroxides, and in particular sodium or potassium hydroxide.

Suitable example of protecting groups $R^7$ are listed in T. W. Green, Protecting Groups in Organic Synthesis, J. Wiley and Sons, 1991 and in particular are those designated as nitrogen-protection groups.

Particular examples of protecting groups $R^7$ are groups of sub-formula (i)

(i)

where $R^8$ is a hydrocarbyl or heterocyclic group, either of which may be optionally substituted.

As used herein, the expression "hydrocarbyl" includes any structure comprising carbon and hydrogen atoms. For example, these may be alkyl, alkenyl, alkynyl, aryl such as phenyl or napthyl, arylalkyl such as benzyl, or cycloalkyl, cycloalkenyl or cycloalkynyl. Suitably hydrocarbyl groups contain up to 20 and preferably up to 10 carbon atoms.

The term "aryl" refers to aromatic rings such as phenyl or naphthyl.

The term "heterocyclic" includes aromatic or non-aromatic rings, for example containing from 4 to 20, suitably from 5 to 8 ring atoms, at least one of which, and suitably from 1 to 4 of which is a heteroatom such as oxygen, sulphur or nitrogen. They may be monocyclic or have fused rings, such a bicyclic or tricyclic ring systems. Examples of such groups include furyl, thienyl, pyrrolyl, pyrrolidinyl, imidazolyl, triazolyl, thiazolyl, tetrazolyl, oxazolyl, isoxazolyl, piperidinyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

The term "heteroaryl" refers to heterocyclic groups which are aromatic in nature. Thus these may comprises cyclic aromatic hydrocarbons in which one or more carbon atoms have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, qunioliziinyl, isoquinolyl, quinolyl phthalazinyl, naphthyridinyl, quinoxalinyl, isothiazolyl and benzo[b]thienyl. Preferred heteroaryl groups are five or six membered rings and contain from one to three heteroatoms.

Suitable optional substituents for heterocyclic and hydrocarbyl groups $R^8$ include nitro, cyano, halo, oxo, $=CR^{13}R^{14}$, $C(O)_xR^{12}$, $OR^{12}$, $S(O)_yR^{12}$, $NR^{13}R^{14}$, $C(O)NR^{13}R^{14}$, $OC(O)NR^{13}R^{14}$, $=NOR^{12}$, $-NR^{12}C(O)_xR^{13}$, $-NR^{12}CONR^{13}R^{14}$, $-N=CR^{13}R^{14}$, $S(O)_yNR^{13}R^{14}$ or $-NR^{12}S(O)_yR^{13}$ where $R^{12}$, $R^{13}$ and $R^{14}$ are independently selected from hydrogen or optionally substituted hydrocarbyl, or $R^{13}$ and $R^{14}$ together form an optionally substituted ring which optionally contains further heteroatoms such as $S(O)_y$ oxygen and nitrogen, x is an integer of 1 or 2, y is 0 or an integer of 1-3. Hydrocarbyl groups $R^8$ may also include heterocyclic substituents, which may themselves be optionally substituted by one or more of the optional substituents listed above. Heterocyclic groups may also be substituted with hydrocarbyl groups which may also be optionally substituted by any of the groups listed above.

Preferably $R^8$ is a hydrocarbyl group such as alkyl, aryl or arylalkyl. Most preferably $R^8$ is a straight chain alkyl group of from 1 to 6 carbon atoms, and particularly is a straight chain $C_{1-4}$alkyl group, such as methyl.

Particular examples of groups $R^4$ and $R^5$ are hydrogen, halo, nitro, cyano, fluoromethyl, difluoromethyl, trifluoromethyl, trifluoromethoxy, carboxy, carbamoyl, sulphamoyl, ureido, $C_{1-6}$alkyl, $C_{2-6}$alkenyl, $C_{2-6}$alkynyl, $C_{1-6}$alkoxy, $C_{1-6}$alkanoyl and $C_{1-6}$alkanoyloxy.

Suitably $R^4$ and $R^5$ are independently selected from hydrogen, halo, nitro, cyano, fluoromethyl, difluoromethyl, trifluoromethyl, trifluoromethoxy, carboxy, carbamoyl, sulphamoyl, $C_{1-4}$alkyl, $C_{2-4}$alkenyl, $C_{2-4}$alkynyl, $C_{1-4}$alkoxy, $C_{1-4}$alkanoyl, and $C_{1-4}$alkanoyloxy.

Preferably $R^4$ and $R^5$ are independently selected from hydrogen and halogen such as chlorine, fluorine and bromine, and in particular chlorine.

Most preferably $R^4$ is hydrogen and $R^5$ is halogen such as chlorine.

Particular examples of protecting groups $R^6$ are any organic groups which can be removed by hydrogenation or hydrolysis. These include optionally substituted hydrocarbyl or optionally substituted heterocyclic groups. Such groups may be similar to those listed above in relation to $R^7$.

Suitable example of protecting groups $R^6$ are also listed in T. W. Green, Protecting Groups in Organic Synthesis, J. Wiley and Sons, 1991 and in particular are those designated as acid protecting groups.

In particular $R^6$ is a hydrocarbyl group such as $C_{1-6}$alkyl, $C_{2-6}$alkenyl, $C_{2-6}$alkynyl, aryl such as phenyl, or arylalkyl such as benzyl.

Conversion of a protecting group $R^6$ to hydrogen is suitably effected using conventional methods, for example as described in WO 02/20530. In particular, the compound is reacted with a base such as lithium hydroxide, in an organic solvent such as methanol, at temperatures of from 20-80° C., and conveniently at the reflux temperature of the solvent.

Compounds of formula (II) are suitably prepared by reacting a compound of formula (III)

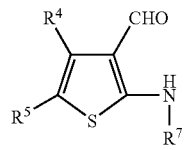

(III)

where $R^4$ and $R^5$ are as defined in relation to formula (I), and $R^6$ and $R^7$ are as defined in relation to formula (II), with a compound of formula (IV):

$LCH_2COOR^6$ (IV)

where L is a leaving group such as halogen and in particular bromine. The reaction is suitably effected in the presence of a base in an organic solvent such as dimethylformamide, N-methylpyrrolidone (NMP) or acetone. Suitable bases include alkali metal carbonates, bicarbonates, hydroxides, or methoxides, but are preferably weak bases such as alkali metal carbonates or bicarbonates, for instance potassium bicarbonate. The reaction may be conducted at elevated temperatures, for example of from 30 to 100° C. depending on the solvent used. For example when dimethylformamide is the solvent, the reaction is preferably carried out from 50 to 70° C. and most preferably at about 60° C. When NMP is the solvent, the reaction may be carried out from 30 to 50° C., preferably at about 40° C.

Compounds of formula (III) are suitably prepared by formylation of a compound of formula (V)

(V)

where $R^4$ and $R^5$ are as defined above in relation to formula (I) and $R^7$ is as defined above in relation to formula (II). This can be carried out using conventional methods such as the Vilsmeier-Haack reaction. In this reaction, the compound of formula (V) is reacted with a formyl containing reagent such as a compound of formula (VI)

(VI)

where $R^9$ and $R^{10}$ are independently selected from phenyl and alkyl groups (in particular lower alkyl groups of 1 to 4 carbon atoms, such as methyl) in the presence of phosphorus oxychloride. The reaction is suitably effected at moderate temperatures and conveniently at room temperature. The compound of formula (VI) may act as a solvent also, where it is for example, DMF, alternatively a different organic solvent may be used, such as dichloromethane.

The applicants have found however that under some conditions this reaction produces a significant proportion of an amidine of formula (VII)

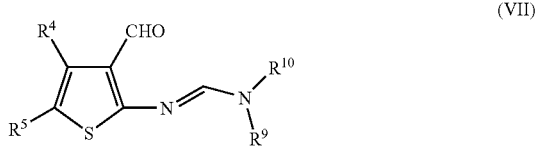

(VII)

where $R^4$ and $R^5$ are as defined in relation to formula (I) and $R^9$ and $R^{10}$ are as defined in relation to formula (VI). A compound of formula (VII) may be converted to a compound of formula (III) by reaction with a compound of formula (VIII)

$(R^7)_2O$     (VIII)

where $R^7$ are as defined in relation to formula (II), under acidic conditions, for example in a solvent comprising an organic acid, such as acetic acid. Elevated temperatures for example of from 80-150° C. and preferably from 110-130° C. are employed. Conveniently the reaction may be effected at the reflux temperature of the solvent. Particular examples of compounds of formula (VIII) are those where groups $R^7$ are groups of sub-formula (i) as defined above, and in particular where $R^8$ is methyl, so that the compound of formula (VIII) is acetic anhydride.

Generally, where the compound of the formula (V) is reacted with the formyl containing compound of the formula (VI) using a solvent such as dichloromethane, an amidine of formula (VII) is not formed in significant quantities, and the desired compound of the formula (III) is instead obtained in good yield.

Compounds of formula (V) are suitably prepared by reacting a compound of formula (IX)

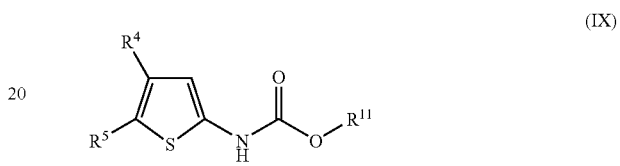

(IX)

where $R^4$ and $R^5$ are as defined above in relation to formula (I), and $R^{11}O(C=O)$ is a labile nitrogen-protecting group, with a compound of formula (VIII) as defined above, under acidic conditions, for example in a solvent comprising an organic acid, such as acetic acid. Elevated temperatures for example of from 80-150° C. and preferably from 110-130° C. are employed. Conveniently the reaction may be effected at the reflux temperature of the solvent.

Suitable labile nitrogen protecting groups for $R^{11}O(C=O)$ include tertiary-butoxy carbonyl groups, or benzyloxycarbonyl groups.

Compounds of formula (IX) are either known (see for example Binder et al., Synthesis, (1977, (4) 255-6) or can be prepared from known compounds. In particular, compounds of formula (IX) are suitably prepared by subjecting a compound of formula (X)

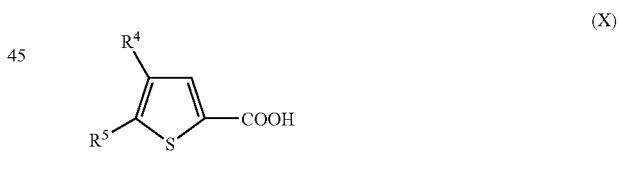

(X)

where $R^4$ and $R^5$ are as defined in relation to formula (I), to a Curtius rearrangement reaction, in the presence of an alcohol of formula $R^{11}OH$. In this reaction, the compound of formula (X) is reacted with an diphenylphosphorylazide, to convert the acid group to a carbonyl azide, which is thermally decomposed to the amide via an isocyanate. Suitable reaction conditions are illustrated hereinafter.

Compounds of formula (II), (III) and (VII) are novel and form further aspects of the invention.

Compounds of formula (IV), (V), (VI), (VIII), (IX) and (X) are known compounds or they can be prepared from known compounds by conventional methods.

Compounds of formula (I) are suitably used in the production of pharmaceutical compounds and in particular, compounds with glycogen phosphorylase activity as described in WO 02/20530 and EP-A-1088824.

Thus in a further aspect, the invention provides a method as described above, for the production of a compound of formula (I) where $R^6$ is hydrogen, and further comprising reacting the compound of formula (I) obtained with an amine of formula (XI),

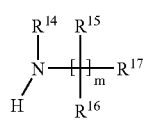
(XI)

where $R^{14}$ is selected from hydrogen or $C_{1-8}$alkyl,
m is an integer of from 0 to 4,
each $R^{15}$ is the same or different and is selected from hydrogen, halo, nitro, cyano, hydroxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-4}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, $C_{3-8}$cycloalkyl$C_{1-6}$alkyl, aryl, aryl$C_{1-6}$alkyl, heterocyclic group and (heterocyclic group)$C_{1-6}$alkyl; wherein $R^{15}$ may be optionally substituted on carbon by one or more groups selected from P and wherein if said heterocyclic group contains an —NH— moiety that nitrogen may be optionally substituted by a group selected from R;
each $R^{16}$ is the same or different and is selected from hydrogen and $C_{1-6}$alkyl;
$R^{17}$ is selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl) amino, N,N—($C_{1-6}$alkyl)$_2$amino, $C_{1-6}$alkanoylamino, N—($C_{1-6}$alkyl)carbamoyl, N,N—($C_{1-4}$alkyl)$_2$carbamoyl, N—($C_{1-6}$alkyl)-N—($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, sulphamoylamino, N—($C_{1-6}$alkyl)sulphamoylamino, N,N—($C_{1-6}$alkyl)$_2$sulphamoylamino, $C_{1-6}$alkylsulphonylamino, $C_{1-6}$alkylsulphonylaminocarbonyl, $C_{1-6}$alkylsulphonyl-N—($C_{1-6}$alkyl)amino and a group -E-F-G-H;
wherein E and G are independently selected from a direct bond, —O—, —S—, —SO—, —SO$_2$—, —OC(O)—, —C(O)O—, —C(O)—, —NR$^a$—, —NR$^a$C(O)—, —C(O)NR$^a$—, —SO$_2$NR$^a$—, —NR$^a$SO$_2$—, —NR$^a$C(O)NR$^b$—, —OC(O)NR$^a$—, —NR$^a$C(O)O—, —NR$^a$SO$_2$NR$^b$—, —SO$_2$NR$^a$C(O)— and —C(O)NR$^a$SO$_2$—; wherein R$^a$ and R$^b$ are independently selected from hydrogen and $C_{1-6}$alkyl which is optionally substituted by a group V;
F is $C_{1-6}$alkylene optionally substituted by one or more Q or a direct bond;
H is selected from aryl, $C_{3-8}$cycloalkyl and heterocyclic group; wherein H may be optionally substituted on carbon by one or more groups selected from S and wherein if said heterocyclic group contains an —NH— moiety that nitrogen may be optionally substituted by a group selected from T;
P, S and Q are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N—($C_{1-6}$alkyl)-N—($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, aryl and heterocyclic group; wherein P, S and Q may be optionally and independently substituted on carbon by one or more groups selected from V and wherein if said heterocyclic group contains an —NH— moiety that nitrogen may be optionally substituted by a group selected from U;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

R, T and U are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, phenyl, benzyl, benzyloxycarbonyl, benzoyl and phenylsulphonyl wherein R, T and U may be optionally and independently substituted on carbon by one or more groups selected from V;

to produce a compound of formula (XII)

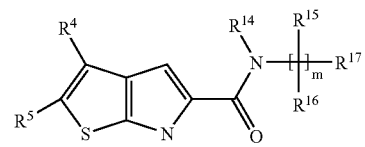
(XII)

where $R^4$, $R^5$, $R^{15}$, $R^{16}$, $R^{17}$ and m are as defined above, or a pharmaceutically acceptable salt or an in vivo hydrolysable ester thereof.

Particular examples of compounds of formula (XII) are compounds where $R^{14}$ is hydrogen, as described in WO 02/20530. For instance, suitable compounds of formula (XII) are compounds where $R^4$ and $R^5$ are as defined above, $R^{14}$ is hydrogen, m is 0 and $R^{17}$ is a group -E-F-G-H;

wherein E, F and G are each a direct bond;

H is a $C_{3-12}$cycloalkyl which is optionally fused to a benz ring wherein H may be optionally substituted on carbon by one or more groups S which are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl) amino, N,N—($C_{1-6}$alkyl)$_2$amino, $C_{1-6}$alkanoylamino, N—($C_{1-6}$alkyl)carbamoyl, N,N—($C_{1-6}$alkyl)2carbamoyl, N—($C_{1-6}$alkyl)-N—($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, aryl and heterocyclic groups; wherein S may be optionally substituted on carbon by one or more groups selected from V;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

or a pharmaceutically acceptable salt thereof.

Other suitable compounds of formula (XII) are compounds where $R^4$ and $R^5$ are as defined above, $R^{14}$ is hydrogen, m is 0, and $R^{17}$ is a group -E-F-G-H;

wherein E, F and G are each a direct bond; and

H is a cyclic amide of formula

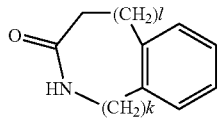

in which the point of attachment is the carbon atom adjacent to the carbonyl group, k is 0, 1 or 2 and 1 is 0, 1 or 2 such that the sum of (k+1) is 1, 2 or 3 and wherein one of the carbon atoms governed by k or 1 may be replaced by sulphur and wherein H is optionally substituted on the carbon atom adjacent to the aromatic ring by a group selected from S and may be independently optionally substituted on nitrogen by a group selected from T;

S is selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N—($C_{1-6}$alkyl)-N—($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, aryl and heterocyclic group; wherein S may be optionally and independently substituted on carbon by one or more groups selected from V and wherein if said heterocyclic group contains an —NH— moiety that nitrogen may be optionally substituted by a group selected from U;

T and U are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, phenyl, benzyl, benzyloxycarbonyl, benzoyl and phenylsulphonyl wherein R, T and U may be optionally and independently substituted on carbon by one or more groups selected from V;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl and 4-hydroxypiperidinocarbonyl;

or a pharmaceutically acceptable salt or an in vivo hydrolysable ester thereof.

Yet further examples of compounds of formula (XII) are compounds where $R^{14}$ is hydrogen, and wherein $R^4$ and $R^5$ are independently selected from hydrogen, halo or $C_{1-6}$alkyl, m is 1; $R^{15}$ is hydrogen or aryl$C_{1-6}$alkyl, $R^{16}$ is hydrogen or $C_{1-6}$alkyl, and $R^{17}$ is selected from a group -E-F-G-H; wherein E, F and G are each a direct bond;

H is an unsaturated five membered heterocyclic group containing at least one nitrogen atom and one or two ring atoms selected from oxygen and sulphur and wherein H may be optionally substituted on carbon by one or more groups S which are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$allyl)$_2$carbamoyl, N—($C_{1-6}$alkyl)-N—($C_{1-6}$alkoxy)carbamoyl, $C_{1-6}$allylS(O)$_a$ wherein a is 0 to 2, $C_{1-6}$alkoxycarbonyl, $C_{1-6}$alkoxycarbonylamino, N—($C_{1-6}$allyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl and aryl groups;

or a pharmaceutically acceptable salt thereof.

Other particular examples include compounds of formula (XII) where $R^{14}$ is hydrogen, $R^4$ and $R^5$ are independently selected from hydrogen, halo or $C_{1-6}$alkyl.

m is 0; and $R^{17}$ is a group -E-F-G-H;

wherein E is a direct bond;

F is methylene;

wherein G is —C(O)NR$^a$—, wherein R$^a$ is selected from hydrogen or $C_{1-6}$alkyl which is optionally substituted by a group V;

H is aryl which may be optionally substituted on carbon by one or more groups selected from S;

S is selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N—($C_{1-6}$alkyl)-N—($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, aryl and heterocyclic group; wherein S may be optionally and independently substituted on carbon by one or more groups selected from V;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N- ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

or a pharmaceutically acceptable salt thereof.

Other particular compounds of formula (XII) are compounds where the group

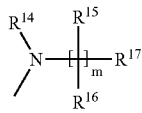

is a group of sub-formula (ii)

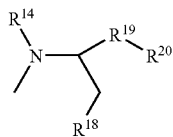

where $R^{14}$ is as defined above, $R^{18}$ is aryl, substituted aryl, heteroaryl, or substituted heteroaryl, $R^{19}$ is a bond or a group —CH(OH)—, and $R^{20}$ is a group —C(=O)-A or a group —CH(OH)—C(=O)-A in which A is $NR^aR^d$, —$NR^aCH_2CH_2OR^a$, or

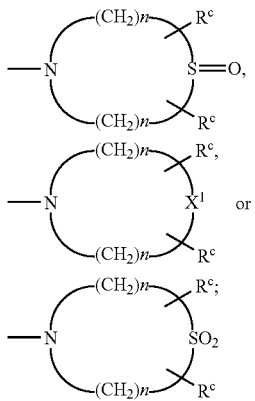

each $R^a$ and $R^b$ is independently hydrogen or —$C_1$-$C_8$alkyl;
each $R^d$ is independently hydrogen, $C_1$-$C_8$alkyl, $C_1$-$C_8$alkoxy, aryl, substituted aryl, heteroaryl, or substituted heteroaryl;
each $R^c$ is independently hydrogen, —C(=O)$OR^a$, —$OR^a$, —$SR^a$, or —$NR^aR^a$; and each n is independently 1-3, and $X^1$ is $NR^a$, —$CH_2$—, O or S.

Examples of substituents for aryl and heteroaryl groups Q and $R^d$ include halogen, $C_{1-8}$alkoxy, $C_{1-8}$alkyl, trifluoromethyl, amino, mono or di-($C_{1-8}$alkyl)amino, nitro, cyano, carboxy or $C_{1-8}$alkyl esters thereof.

The invention will now be particularly described by way of example, in which, unless stated otherwise:

(i) temperatures are given in degrees Celsius (° C.); operations were carried out at room or ambient temperature, that is, at a temperature in the range of 18-25° C. and under an atmosphere of an inert gas such as argon;
(ii) organic solutions were dried over anhydrous magnesium sulphate; evaporation of solvent was carried out using a rotary evaporator under reduced pressure (600-4000 Pascals; 4.5-30 mmHg) with a bath temperature of up to 60° C.;
(iii) chromatography means flash chromatography on silica gel; thin layer chromatography (TLC) was carried out on silica gel plates;
(iv) in general, the course of reactions was followed by TLC and reaction times are given for illustration only;
(v) yields are given for illustration only and are not necessarily those which can be obtained by diligent process development; preparations were repeated if more material was required;
(vi) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent or other solvents (where indicated in the text) including deuterated chloroform $CDCl_3$;
(vii) chemical symbols have their usual meanings; SI units and symbols are used;
(viii) reduced pressures are given as absolute pressures in Pascals (Pa); elevated pressures are given as gauge pressures in bars;
(ix) solvent ratios are given in volume: volume (v/v) terms;
(x) mass spectra (MS) were run with an electron energy of 70 electron volts in the chemical ionisation (CI) mode using a direct exposure probe; where indicated ionisation was effected by electron impact (EI), fast atom bombardment (FAB) or electrospray (ESP); values for m/z are given; generally, only ions which indicate the parent mass are reported and unless otherwise stated the value quoted is (M−H)⁻;

The following abbreviations are used:
DMSO=dimethylsulfoxide
DCM=dichloromethane
TBF is tetrahydrofuran
HPLC is high performance liquid chromatography
DMP is dimethylformamide
TBF is tetrahydrofuran
LCMS is liquid chromatography/mass spectrometry

EXAMPLE 1

Step 1

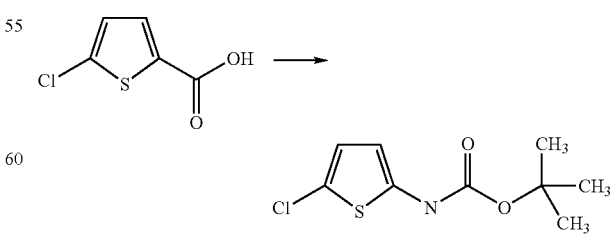

Under argon, 5-chlorothiophene-2-carboxylic acid (5.48 g) was dissolved in warm dry tertiary butanol (34 ml) and triethylamine (4.7 ml) added followed by diphenylphosphorylazide (DPPA) (7.26 ml). The mixture was then heated slowly to reflux and refluxed for about 12 hours.

The reaction mixture was then cooled and poured into H$_2$O (~180 ml). The resultant dark suspension was filtered, and the solid was washed with H$_2$O then dried under suction to a brown powder. This was dissolved in diethyl ether and the solution dried over MgSO$_4$, filtered and evaporated to the desired product, tert-butyl (5-chloro-2-thienyl)carbamate, as a dark brown solid (Yield=6.75 g).

$^1$H NMR (400 MHz, d$^6$-DMSO) 6.82 (d, 1H), 6.34 (d, 1H), 1.50 (s, 9H)

Step 2

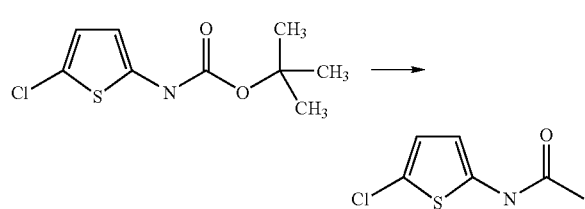

A mixture of acetic anhydride (6.42 ml) in acetic acid (60 ml) was added to the product from step 1 (7.48 g) and the resultant mixture heated at 120° C. for 4 hours. On cooling the reaction mixture was poured into water and extracted with EtOAc. The EtOAc layer was washed with saturated aqueous K$_2$CO$_3$, dried over Na$_2$SO$_4$, filtered and evaporated under reduced pressure to give a black solid. Chromatography through silica using an eluent of CH$_2$Cl$_2$ to Et$_2$O gave N-(5-chloro-2-thienyl)acetamide (4.63 g, 83%) as a pale brown solid. $^1$H NMR (400 MHz, d$^6$-DMSO) 11.33 (br s, 1H), 6.82 (d, 1H), 6.40 (d, 1H), 2.05 (s, 3H); ESP$^-$ 174.29

Step 3

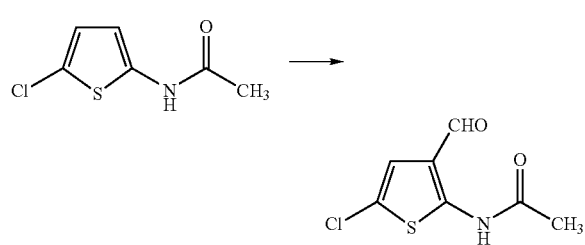

The product from step 2 (1.09 g) was dissolved in dimethyl formamide (DMF) (3 ml) and cooled in an ice bath. POCl$_3$ (0.58 ml) was added dropwise and the dark mixture stirred at 0° C. for 30 minutes then allowed to warm to room temperature, and stirred at room temperature for 64 hours.

The reaction mixture was poured into ice water and the aqueous phase was extracted into dichloromethane. The dichloromethane layer was dried over MgSO$_4$, filtered and evaporated to a black gum. Purification was effected by suction column chromatography though silica using hexane as initial eluent and CH$_2$Cl$_2$ to apply the material to the top of the column. The concentration of diethyl ether was slowly increased (10% jumps) to neat diethyl ether. Several fractions were analysed by LCMS. The 2 fractions which had (MH)+ at 217 and (MH)$^-$ at 202 were combined. They were evaporated to give a yellow solid (0.53 g). Spectral analysis both by LCMS and $^1$H NMR showed that this was a mixture of the desired N-(5-chloro-3-formyl-2-thienyl)acetamide (87%) and N'-(5-chloro-3-formyl-2-thienyl)-N,N-dimethylimidoformamide (13%).

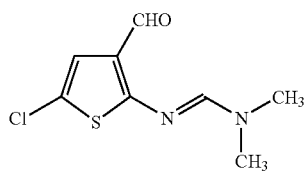

$^1$H NMR N-(5-chloro-3-formyl-2-thienyl)acetamide (300 MHz, d$^6$-DMSO) 11.65 (br s, 1H), 9.93 (s, 1H), 7.22 (s, 1H), 2.25 (s, 3); ESP$^-$ 202.21;

N'-(5-chloro-3-formyl-2-thienyl)-N,N-dimethylimidoformamide (300 MHz, d$^6$-DMSO) 9.90 (s, 1H), 7.97 (s, 1H), 6.93 (s, 1H), 3.13 (s, 3H), 3.02 (s, 3H); ESP$^+$ 217.22

Step 4

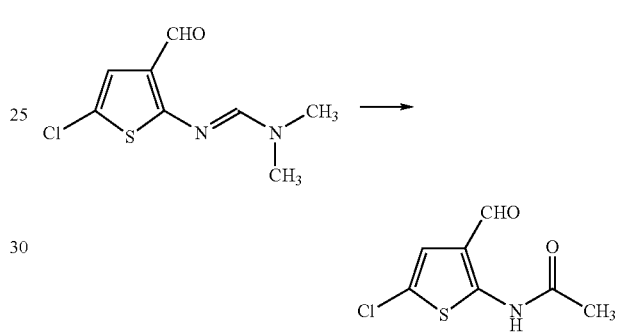

The mixture from Step 3 (0.53 g) was dissolved in acetic acid (5 ml) and to this was added acetic anhydride (0.5 ml) followed by H$_2$O (0.25 ml). The mixture was heated to reflux for approximately 1 hour whereupon tlc analysis indicated that none of the dimethyl amidine derivative remained.

The reaction mixture was poured into H$_2$O and the precipitate filtered. The aqueous phase was extracted into a mixture of dichloromethane and methanol in a ratio of 19:1 and the precipitate was dissolved in a similar mixture. The combined organic solutions were washed with dilute aqueous potassium carbonate, ensuring that the pH remained at about 12, then dried over MgSO$_4$. Filtration and evaporation under reduced pressure gave the desired product, N-(5-chloro-3-formyl-2-thienyl)acetamide, as a yellow, orange solid (Yield=0.53 g).

$^1$H NMR (300 MHz, d$^6$-DMSO) 11.65 (br s, 1H), 9.93 (s, 1H), 7.22 (s, 1H), 2.25 (s, 3H); ESP$^-$ 202.21

Alternative Step 3 (Removing Need for Step 4)

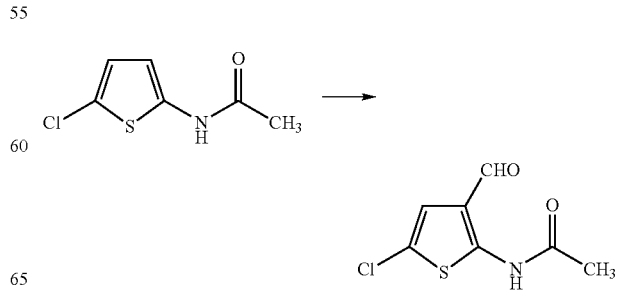

Dichloromethane (7 ml), POCl₃ (2.24 ml) and DMF (3.10 ml) were stirred at room temperature for 15 minutes to form a clear solution. The product from step 2 (3.50 g) was dissolved in dichloromethane (70 ml) and added via syringe pump to the POCl₃/DMF solution over a period of 1.5 hours to form a dark solution. The reaction was stirred at room temperature for 23 hours. Saturated sodium bicarbonate (200 ml) was added gradually to the reaction mixture, until pH 8 was obtained. The organic phase was separated and sodium hydroxide (1M, 150 ml and 2M, 100 ml) was added slowly to the solution in an ice bath, until pH 14 was obtained. The aqueous layers were combined and hydrochloric acid (2M, 150 ml) was added until pH 3 was obtained. The product was extracted into ethyl acetate (150 ml) and washed with brine (25 ml). The solvent was evaporated to give N-(5-chloro-3-formyl-2-thienyl)acetamide (2.09 g, 52%) as a dark grey solid.

¹H NMR (400 MHz, CDCl₃) 11.37 (br s, 1H), 9.69 (s, 1H), 7.01 (s, 1H), 2.31 (s, 1H)

Step 5

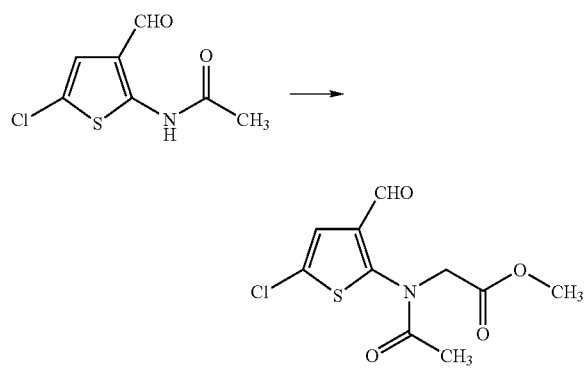

The product from Step 4 (460 mg) was placed under argon, in dry glassware, and dissolved in dry DMF (2 ml). Potassium bicarbonate (567 mg) was added to the solution followed by methylbromoacetate (0.54 ml). The mixture was heated to 40° C. for 150 mins, and then at 60° C. for a further 120 mins. The reaction was stirred at room temperature overnight at again heated at 60° C. for 270 minutes on the next day.

The product was partitioned between dichloromethane and water and the dichloromethane layer was dried over MgSO₄, filtered and evaporated under reduced pressure to give a dark oil. This was purified by suction column chromatography through silica using hexane as initial eluent and CH₂Cl₂ to apply the material to the top of the column. The concentration of CH₂Cl₂ was increased (10% increments, 50 ml fractions) to 100% CH₂Cl₂, held at CH₂Cl₂ for a few fractions then the concentration of Et₂O increases (1% increments) until the spots were removed from the column. The spot corresponding to the desired methyl N-acetyl-N-(5-chloro-3-formyl-2-thienyl)glycinate (identified using LCMS) was collected for use in the subsequent step.

¹H NMR (300 MHz, d⁶-DMSO) 9.93 (s, 1H), 7.20 (s, 1H), 4.40 (br s, 2H), 3.77 (s, 3H), 2.06 (s, 3H).

Alternative Step 5

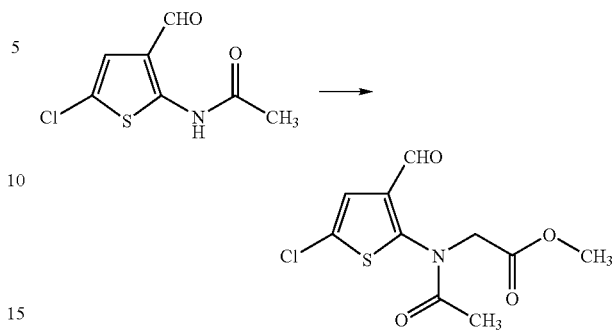

The product from Step 4 (1.50 g) was placed under argon, in dry glassware, and dissolved in dry NMP (10 ml). Potassium bicarbonate (2.96 g) was added to the solution followed by NMP (5 ml), methyl-bromoacetate (2.79 ml) and tert-butyl methyl ether (0.5 ml). The mixture was heated to 40° C. for 23 hours. The product was partitioned between EtOAc and water and the EtOAc layer was dried over MgSO₄, filtered and evaporated under reduced pressure to give an orange oil. This was purified by suction column chromatography through silica using CH₂Cl₂ as initial eluent and to apply the material to the top of the column. The concentration of Et₂O increased (0.25% increments) to give after evaporation the product methyl N-acetyl-N-(5-chloro-3-formyl-2-thienyl)glycinate (1.20 g, 59%) as a clear, yellow gum.

¹H NMR (300 MHz, d⁶-DMSO) 9.93 (s, 1H), 7.20 (s, 1H), 4.40 (br s, 2H), 3.77 (s, 3H), 2.06 (s, 3H)

Step 6

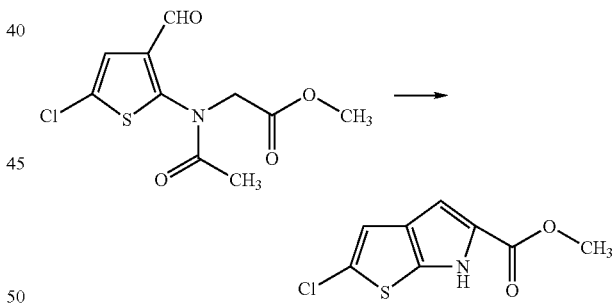

The product from Step 5 (170 mg) was dissolved in MeOH under an argon atmosphere, and a solution of sodium methoxide in methanol (0.62 ml of 25% solution) added causing a slight darkening to a brown, clear solution. The mixture was refluxed for about 1 hour.

The reaction mixture was partitioned between dichloromethane and water, and the dichloromethane layer was dried over MgSO₄, filtered and evaporated under reduced pressure to give the desired product, methyl 2-chloro-6H-thieno[2,3-b]pyrrole-5-carboxylate as a yellow solid (Yield=97 mgs (93%). The structure was confirmed by LCMS and ¹HNMR spectroscopy. ¹H NMR (300 MHz, d⁶-DMSO) 9.40 (br s, 1H), 6.91 (s, 1H), 6.82 (s, 1H), 3.82 (s, 3H); ESP⁻ 214.16

Alternative Step 6

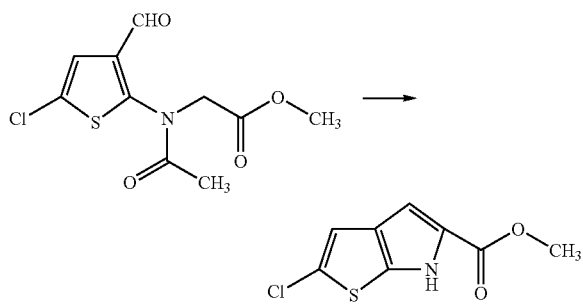

The product from Step 5 (1.20 g) was dissolved in DMF (15 ml), $K_2CO_3$ (631 mg) added and the mixture heated to 60° C. for 90 minutes. On cooling to room temperature the mixture was poured into water (30 ml) and the white solid filtered off and washed with water to give the desired product, methyl 2-chloro-6H-thieno[2,3-b]pyrrole-5-carboxylate (741 mg, 79%) as an off white solid. $^1$H NMR (300 MHz, d$^6$-DMSO) 9.40 (br s, 1H), 6.91 (s, 1H), 6.82 (s, 1H), 3.82 (s, 3H); ESP$^-$ 214.16

The invention claimed is:

1. A process for preparing a compound of formula (I)

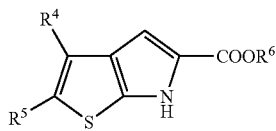

wherein
$R^4$ and $R^5$ are independently selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N,—($C_{1-6}$alkyl)$_2$sulphamoyl, $C_{1-6}$alkylsulphonylamino, and $C_{1-6}$alkylsulphonyl-N—($C_{1-6}$alkyl)amino; and
$R^6$ is hydrogen or a protecting group,
which process comprises cyclisation of a compound of formula (II)

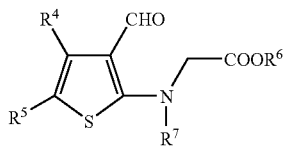

wherein
$R^4$, $R^5$, and $R^6$ are as defined in relation to formula (I); and
$R^7$ is a nitrogen protecting group; and
removing protecting group $R^7$, and thereafter if desired or necessary, removing any protecting group $R^6$ to obtain the corresponding carboxylic acid.

2. A process according to claim 1, wherein the protecting group $R^7$ is removed during the cyclisation.

3. A process according to claim 1, wherein in a structure of formula (II), $R^7$ is a group of sub-formula (i)

wherein $R^8$ is a straight chain alkyl group of from 1 to 6 carbon atoms.

4. A process according to claim 1, wherein $R^4$ and $R^5$ are independently selected from hydrogen, halo, nitro, cyano, fluoromethyl, difluoromethyl, trifluoromethyl, trifluoromethoxy, carboxy, carbamoyl, sulphamoyl, $C_{1-4}$alkyl, $C_{2-4}$alkenyl, $C_{2-4}$alkynyl, $C_{1-4}$alkoxy, $C_{1-4}$alkanoyl, and $C_{1-4}$alkanoyloxy.

5. A method according to claim 1, for the production of a second compound of formula (I) where $R^6$ is hydrogen, further comprising reacting a first compound of formula (I) with an amine of formula (XI),

where $R^{14}$ is selected from hydrogen and $C_{1-8}$alkyl;
m is an integer of from 0 to 4;
each $R^{15}$ is the same or different and is selected from hydrogen, halo, nitro, cyano, hydroxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$ alkyl)$_2$amino, $C_{1-6}$alkanoylamino, N—($C_{1-6}$alkyl)carbamoyl, N,N—($C_{1-4}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$ alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, $C_{3-8}$cycloalkyl$C_{1-6}$alkyl, aryl, aryl$C_{1-6}$alkyl, heterocyclic group, and (heterocyclic group)$C_{1-6}$alkyl; wherein $R^{15}$ may be optionally substituted on carbon with one or more P groups, and if said heterocyclic group contains an —NH— moiety, that nitrogen may be optionally substituted with an R group;
each $R^{16}$ is the same or different and is selected from hydrogen and $C_{1-6}$alkyl;
$R^{17}$ is selected from hydrogen, halo, nitro, cyano, hydroxy, fluoromethyl, difluoromethyl, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$ amino, $C_{1-6}$alkanoylamino, N—($C_{1-6}$alkyl)carbamoyl, N,N—($C_{1-4}$alkyl)$_2$carbamoyl, N—($C_{1-6}$alkyl)-N—($C_{1-6}$alkoxy)carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$ alkyl)$_2$sulphamoyl, sulphamoylamino, N—($C_{1-6}$ alkyl)sulphamoylamino, N,N—($C_{1-6}$alkyl)$_2$sulphamoylamino, $C_{1-6}$alkylsulphonylamino, $C_{1-6}$alkylsulphonylaminocarbonyl, $C_{1-6}$alkylsulphonyl-N—($C_{1-6}$alkyl)amino, and a group -E-F-G-H;

E and G are independently selected from a direct bond, —O—, —S—, —SOS—, —SO$_2$—, —OC(O)—, —C(O)O—, —C(O)—, —NR$^a$—, —NR$^a$C(O)—, —C(O)NR$^a$—, —SO$_2$NR$^a$—, —NR$^a$SO$_2$—, —NR$^a$C(O)NR$^b$—, —OC(O)NR$^a$—, —NR$^a$C(O)O—, —NR$^a$SO$_2$NR$^b$—, —SO$_2$NR$^a$C(O)—, and —C(O)NR$^a$SO$_2$—; R$^a$ and R$^b$ are independently selected from hydrogen and $C_{1-6}$alkyl which is optionally substituted with a V group;

F is $C_{1-6}$alkylene optionally substituted by one or more Q or a direct bond;

H is selected from aryl, $C_{3-8}$cycloalkyl, and heterocyclic group; wherein H may be optionally substituted on carbon with one or more S groups, and if said heterocyclic group contains an —NH— moiety, that nitrogen may be optionally substituted with a T group;

P, S, and Q are independently selected from halo, nitro, cyano, hydroxy, trifluoromethyl, trifluoromethoxy, amino, carboxy, carbamoyl, mercapto, sulphamoyl, ureido, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, N—($C_{1-6}$alkyl)-N—($C_{1-6}$alkoxy)carbamoyl, $C_{1-6}$alkylS(0)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, $C_{3-8}$cycloalkyl, aryl, and heterocyclic group; wherein P, S, and Q may be optionally independently substituted on carbon with one or more V groups and if said heterocyclic group contains an —NH— moiety, that nitrogen may be optionally substituted by a U group;

V is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methyithia, ethyithia, methylsuiphinyl, ethylsuiphinyl, mesyl, ethylsuiphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, morpholino, morpholinocarbonyl, N-benzylcarbamoyl, and 4-hydroxypiperidinocarbonyl;

R, T, and U are independently selected from $C_{1-4}$alkyl, $C_{1-4}$alkanoyl, $C_{1-4}$alkylsulphonyl, $C_{1-4}$alkoxycarbonyl, carbamoyl, N—($C_{1-4}$alkyl)carbamoyl, N,N—($C_{1-4}$alkyl)carbamoyl, phenyl, benzyl, benzyloxycarbonyl, benzoyl, and phenylsulphonyl; wherein R, T, and U may be optionally independently substituted on carbon with one or more V groups; to produce a compound of formula (XII)

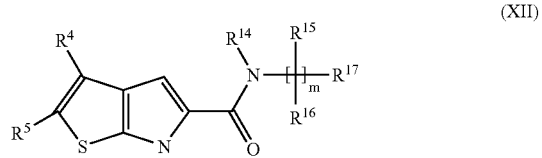

(XII)

where $R^4$, $R^5$, $R^{15}$, $R^{16}$, $R^{17}$, and m are as defined above, or a pharmaceutically acceptable salt or an in vivo hydrolysable ester thereof.

* * * * *